United States Patent [19]

Harper

[11] 4,312,778
[45] Jan. 26, 1982

[54] MEMBRANE SEPARATION OF CATALYST METALS FROM AROMATIC ACID PRODUCTION

[75] Inventor: Jon J. Harper, Naperville, Ill.

[73] Assignee: Standard Oil Company (Indiana), Chicago, Ill.

[21] Appl. No.: 192,914

[22] Filed: Oct. 1, 1980

[51] Int. Cl.³ ............................................. B01D 13/00
[52] U.S. Cl. ............................ 252/410; 252/411 R; 75/101 BE; 423/21.5; 423/50; 423/140
[58] Field of Search ............ 562/414; 210/638, 321.1, 210/649, 650; 423/21.5, 50, 140; 75/101 BE; 252/410, 411

[56] References Cited

U.S. PATENT DOCUMENTS

| | | | |
|---|---|---|---|
| 3,454,490 | 7/1969 | Wallace | 210/638 |
| 3,718,583 | 2/1973 | Wu et al. | 210/638 |
| 3,957,504 | 5/1976 | Win-Sow et al. | 210/638 |
| 4,051,230 | 9/1977 | Miyauchi | 75/101 BE |

*Primary Examiner*—Jacqueline V. Howard
*Attorney, Agent, or Firm*—Fred R. Ahlers; William T. McClain; William H. Magidson

[57] ABSTRACT

Precipitation-free recovery of catalyst metal content of residue from manufacture of benzene carboxylic acid by oxidation with source of molecular oxygen of liquid methyl-substituted benzene in presence of cobalt, manganese, cerium, and mixtures of two or more thereof followed by removal of benzene carboxylic acid and, if used, reaction solvent. Such precipitation-free method comprises extracting such residue with water, contacting the resulting extract solution or suspension of insolubles in extract solution with one side of a cation permeable fluoropolymer membrane and contacting the opposite side of the membrane with a hydrohalidic acid.

7 Claims, No Drawings

MEMBRANE SEPARATION OF CATALYST METALS FROM AROMATIC ACID PRODUCTION

This invention relates to the separation of catalyst metals from fluids produced during the manufacture of benzene carboxylic acids and more particularly pertains to such separation of metals by the use of a hydro-halidic acid, a permeable membrane and a fluid residue obtained after substantial benzene carboxylic acid recovery and, if oxidation reaction solvent is used, its substantial removal.

STATE OF THE ART

No publication has been found which discloses or even suggests the use of a permeable membrane for the separation of metal oxidation from a fluid residue obtained from the manufacture of a benzene carboxylic acid (i.e., benzoic acid, one of the phthalic acids or one of the benzene tricarboxylic acids).

In general, the separation of metal oxidation catalysts cobalt, manganese or cobalt and manganese from such fluid residue disclosed in publications have been by precipitation of the catalyst metals as carbonates from the residue or aqueous extract thereof, recovery of the metal carbonate precipitate and conversion of the recovered precipitate to the acetate or bromide of the catalyst metal.

U.S. Pat. Nos. 2,964,559; 3,557,173; and 3,673,154 among other patents disclose reclaiming of oxidation metal catalyst cobalt or cobalt and manganese either from the acetic acid mother liquor or a concentrate thereof after separation of such mother liquor and solid iso- or terephthalic acid precipitate from the suspension of such acids in said mother liquor resulting from the liquid phase oxidation of mixed xylenes or m- or p-xylene with air at an elevated temperature above 100° C. in the presence of acetic acid solution of cobalt or cobalt and manganese, generally as their acetates, at an elevated pressure to maintain at least the acetic acid solvent in the liquid phase.

U.S. Pat. No. 2,964,559 teaches that after separating suspended phthalic acids from acetic acid mother liquor and distilling water and acetic acid from said mother liquor leaving a residue, water extraction of the residue reclaims 93% of the cobalt and 94% of the manganese but also extracts 72 mole percent of the phthalic anhydride as the free acid and 80 to 100% of the nickel, iron and chromium present.

U.S. Pat. No. 3,557,173 is concerned with eliminating o-phthalic acid from the cobalt reclaimed from the acetic acid mother liquor. This is done by dehydrating the acetic acid mother liquor (e.g., by addition of acetic anhydride thereto or by distillation of at least 50% of the acetic acid therefrom) whereby anhydrous cobalt acetate precipitates and is recovered by filtration.

U.S. Pat. No. 3,673,154 is concerned with reclamation of cobalt free of iron and chromium. This is done by distilling acetic acid and water from the mother liquor to a pH above 3 (e.g., pH 3.15 to 4.5) which precipitates iron and chromium, removing the Fe and Cr containing precipitate, adding sodium carbonate to precipitate cobalt carbonate and form a soluble form of nickel. Dissolving cobalt carbonate in acetic acid provides the solvent and metal catalyst for the next oxidation of xylene.

Published Japanese Patent Application No. 14,339/71 is also concerned with the rejection of iron group contaminants and oxygen-containing aromatic compounds from reclaimed Co or Co and Mn catalyst metals. This is accomplished by distilling acetic acid from the mother liquor after phthalic acid product separation. The distillation residue is extracted either with water or aqueous alkaline carbonate (e.g., $Na_2CO_3$) solution. The water extract solution is buffered to a pH of 4.5 to precipitate basic iron acetate. The filtrate after removal of the iron acetate precipitate is treated with sodium carbonate to precipitate cobalt and manganese as carbonates. The extraction with aqueous alkaline carbonate leaves a solid residue which, after recovery from the aqueous solution, is dissolved in an inorganic acid. Buffering the acid solution to pH 4–5 with sodium acetate precipitates iron group metals so that after their removal, Co and Mn can be precipitated as carbonates.

British Patent Specification No. 1,413,829 is concerned with the rejection of iron group contaminant corrosion metals from cobalt and manganese reclaimed as their carbonates from residues comprising concentrates derived by distilling acetic acid and water from the acetic acid mother liquor after recovery of suspended iso- or terephthalic acid. Such residues are extracted with water in an amount of from 3 to 5 weight parts per weight part of residue. Such amounts of water at at 80° C. dissolve 90 to 98% of the cobalt and manganese content of the residue and provide an extract solution (after separating insolubles) of pH 3.5–5.0 but dissolve relatively little of the other iron group metals present. High quality cobalt and manganese carbonates can be precipitated from such solution after its pH is adjusted preferably to pH in the range of 7 to 8.1 by the use of sodium carbonate and/or bicarbonate.

Said British Patent also discloses that use of water in weight amount equal to the weight of the residue dissolves at 80° C. only 72 to 81% of Co and 66 to 76% of Mn in the residue.

The foregoing techniques for reclaiming Co and/or Mn, while satisfactory when applied to residues obtained from the production of iso- or terephthalic acid, on their face appear either not applicable to or not suitable for the reclamation of cobalt and manganese from residues obtained from the production of o-phthalic acid or its co-production with trimellitic acid by the respective neat oxidation of liquid o-xylene or liquid mixture of o-xylene and pseudocumene.

It has been discovered in our laboratories that relatively small amounts of water, substantially less than the 16:1 to 17:1 water to residue ratios of U.S. Pat. No. 2,964,559 or the 3:1 to 5:1 water to residue ratios of the British Patent, quite surprisingly will, at temperatures of 75° to 80° C., extract more than 90 weight percent of the catalyst metals and less than 25% of the o-phthalic acid from the residues left after the above preparation and recovery of partially purified intramolecular anhydride products and retain the catalyst metals as solutes even at temperatures of 23° C. to 24° C. It has also been found that, although a substantial amount of the oxygen-containing aromatic impurity compounds were also dissolved by the small amount of water, unexpectedly a substantial proportion of the dissolved impurity compounds could be rejected by diluting the extract solution with additional water without substantial change of operating temperature.

From a search of printed publications directed to separation of metal ions from solutions by means of a permeable membrane, the following have been found and are directed to the separation of metal ions which are not commonly used metal catalysts in the production of benzene carboxylic acids.

For example, published Japanese Patent Application (Kokai) Publication No. 53-18244 published Feb. 20, 1978 discloses the separation of ions of metals such as aluminum, copper, lead, zinc, nickel, and chromium from aqueous solutions resulting from anodizing protection or coloration of fabricated aluminum articles. Such solutions have their pH changed twice and, after each pH change, the solution is contacted with a permeable membrane which permits the metal ions to pass through the membrane and deplete the solution's metal ions concentrations. Such schedule of treatment can be an adjustment of pH to a pH greater than 7, contact of the pH adjusted solution with permeable membrane, collect first metal-depleted solution, adjust its pH to the acidic range (pH less than 7), contact the acidified solution with permeable membrane, and collect second metal-depleted solution.

In "Ion-Exchange Selectivity and Metal Ion Separations with a Perfluorinated Cation-Exchange Polymer" by H. L. Yeager and A. Steck at pages 862–865 of Analytical Chemistry, Vol. 51, No. 7, June 1979; said article describes the use of powdered sample of Nafion-120 (a polymeric perfluorinated sulfonic acid ion exchanger of Du Pont and Co.) for hydrogen ion exchange with alkali metal and silver ions in aqueous solution, sorbed water and cation diffusion. No useful purpose for such metal ion separations was mentioned in said article.

U.S. Pat. No. 4,186,084 issued Jan. 29, 1980 is directed to diaphrams for chloralkali electrolytic cells prepared from fluoropolymers chemically modified with sulfur (e.g., in sufonyl, suffinyl and sulfuryl halide, mercaptons, metal mercaptides, thio acids, metal salts of thio acids esters of mono- and dithio acids) or phosphorus (e.g., in tetrathiophosphoric acid and metal salts thereof; phosphonic acid, metal salts and esters thereof; phosphorous acid and salts thereof; and halides of phosphorous and phosphonic acid). Such diaphrams do effectively separate alkali metal ions from aqueous solutions also containing chlorine ions.

U.S. Pat. No. 3,450,630 is directed to separations of one metal ion from other metal ions by the use in electrolytic cell of electrically uncharged membranes of polymeric matrices having etheric oxygen and/or carbonyl groups. Said polymeric matrices are derived from polyvinyl chloride, copolymers of ethylene and vinyl acetate, copolymer of methyl-methacrylate and vinyl acetate, polyvinyl methylketone, copolymer of vinyl methylketone and vinyl acetate, polyalkyl acrylates, copolymer of methyl isopropylketone and methylmethacrylate, copolymer of methylmethacrylate and butylacrylate, and copolymer of vinyl acetate and acrylonitrile.

U.S. Pat. No. 3,450,631 is directed to separations of metal ions of a preselected species from metal ions of another species having the same charge and similar ionic diameter involving permeating the preselected species through an ion-specific membrane comprising supported polyvinyl chloride polymer film plasticized by an organo-phosphorous compound. Specifically uranium ions were removed from admixture with iron and aluminum ions in aqueous solution by uranium permeation through supported plasticized PVC membrane into water on the other side of the membrane.

U.S. Pat. No. 3,408,315 is directed to the production of a microporous polyamide membrane useful for separation of microorganisms, cells and minute particles from various liquids, gases or for sterilizing biological solutions by filtration of the solution.

U.S. Pat. No. 3,149,179 is directed to the separation of alkyl, oxyalkyl and thioalkyl aluminums from linear olefins by contacting the mixture with a chemically resistant, semi-permeable plastic (e.g., polyolefin such as polyethylene) membrane.

As the above state of the art indicates it is of little or no use for devising a method of separating catalyst metals from residual fluids from benzene carboxylic acid manufacture. Such residual fluids contain methyl-, hydroxymethyl-, formyl-substituted benzene toluene and xylene or benzoic acid, benzaldehyde, or phthalic acid together with the benzene carboxylic acid.

SUMMARY OF THE INVENTION

It has now been discovered that the catalyst metals can be separated from the fluid residue of the manufacture of a benzene carboxylic acid by extracting the fluid residue with water at a temperature of from 25° C. up to 100° C. with from 0.25 up to 6, preferably 0.35 to 3, weight parts of water per weight part of residue and then contacting the extract solution or the suspension of insolubles in said solution with one side of a cation permeable fluoropolymer membrane whose other side is contacted with a hydrohalidic acid such as hydrochloric or hydrobromic acid.

The preferred cation permeable membrane can be a flat film or tubing of a polytetrafluoroethylene modified by sulfonic acid groups attached to chain carbon atoms.

Ions of the catalyst metals pass through the membrane but most of the water soluble aromatic compounds including the carboxylic acid-substituted aromatic compounds do not pass through the membrane. Some of the water solvent for the catalyst metals also passes through the membrane.

Such separation of catalyst metals does not occur when acetic acid, phosphoric acid, sulfuric acid or nitric acid is on the side of the membrane opposite the aqueous extract solution of the aromatic process residue.

The compositions of residues from the manufacture of terephthalic acid by catalytic air oxidation of p-xylene, from the manufacture of isophthalic acid (IA) by catalytic air oxidation of m-xylene and from the manufacture of trimellitic anhydride by the catalytic air oxidation of pseudocumene (1,2,4-trimethylbenzene) are shown in TABLES I and II to follow.

The composition of residue from the neat oxidation of liquid o-xylene with air and the effect of the unique low solvent water to residue ratio are shown in TABLES III and IV, also to follow.

TABLE I

| CHARACTERIZATION OF RESIDUE FROM TEREPHTHALIC ACID MANUFACTURE | | | | |
|---|---|---|---|---|
| Components, In Weight % | Sample Number | | | |
|  | 1 | 2 | 3 | 4 |
| Acetic Acid | 0.22 | 3.23 | 3.74 | 3.24 |
| Phthalic Acids | 45.8 | 31.4 | 33.4 | 26.0 |
| Toluic Acids | 5.2 | 12.3 | 12.8 | 22.6 |
| 4-CBA[1] | 1.05 | 4.56 | 4.82 | 9.1 |
| Benzoic Acid | 20.2 | 27.6 | 26.0 | 19.8 |
| Trimellitic Acid | 5.4 | 4.0 | 4.3 | 3.8 |
| OLB Compounds[2] | 5.4 | 4.1 | 4.4 | 0.9 |
| HB Compounds[3] | 0.26 | 7.5 | 5.8 | 0.4 |
| Cobalt | 0.69 | 0.49 | 0.5 | 1.35 |
| Manganese | 1.79 | 1.22 | 1.3 | 2.48 |

TABLE I-continued

CHARACTERIZATION OF RESIDUE FROM TEREPHTHALIC ACID MANUFACTURE

| Components, In Weight % | Sample Number | | | |
|---|---|---|---|---|
| | 1 | 2 | 3 | 4 |
| Bromine | 2.59 | 1.49 | 1.5 | 2.5 |

[1]"4-CBA" is 4-carboxybenzaldehyde (p-formylbenzoic acid).
[2]"OLB Compounds" are other lower boiling compounds.
[3]"HB Compounds" are higher boiling (higher than trimellitic acid) compounds.

TABLE II

CHARACTERIZATION OF RESIDUES FROM THE MANUFACTURE OF ISO-PHTHALIC ACID AND TRIMELLITIC ANHYDRIDE

| Component, In Weight % | RESIDUE | | |
|---|---|---|---|
| | IA | TMLA | TMA |
| Acetic Acid | 0.11 | 1.58 | 0 |
| Phthalic Acids | 39.8 | 12.3 | 1.0 |
| Toluic Acids | 1.8 | 0 | 0 |
| Aldehydes | 0.09 | 0.53 | 1.4 |
| Benzoic Acid | 24.1 | 0.5 | 0 |
| Trimellitic Acid | 2.5 | 38.6 | 65.2[1] |
| OLB Compounds[2] | 1.7 | 4.7 | 1.9 |
| HB Compounds[3] | 5.3 | 0.94 | 0.4 |
| Cobalt | 0.48 | 1.17 | 2.51 |
| Manganese | 1.27 | 0.28 | 0.87 |
| Bromine | 2.6 | 0.94 | 0.15 |

[1]Trimellitic acid anhydride.
[2]See TABLE I Footnote [2].
[3]See TABLE I Footnote [3].

TABLE III

AQUEOUS EXTRACTION AT 24° C. OF RESIDUE FROM DEHYDRATION AND EVAPORATION OF EFFLUENT FROM NEAT OXIDATION OF ORTHO-XYLENE

| Residue Components | Wt. % of Residue | W/R of 1:1 Selectivity % | W/R of 0.35:1 Selectivity % |
|---|---|---|---|
| Benzoic Acid | 4.4 | 78 | 85 |
| Toluic Acid | 0.5 | 80 | 81 |
| Phthalic Anhydride (Acid) | 68.0 | (23) | (19) |
| Iso- and Terephthalic Acid | 1.4 | 62 | 53 |
| Trimellitic Anhydride (Acid) | 3.9 | (92) | (77) |
| Dicarboxynaphthalene | 0.4 | 95 | 75 |
| Methylcarboxybenzophenone | 3.4 | 92 | 72 |
| Tricarboxybenzophenone | 8.1 | 90 | 74 |
| Bis Carboxyanthraquinone | 0.6 | 85 | 75 |
| Bromine[1] | 1.19 | 95 | 85 |
| Cobalt[1] | 0.47 | 99 | 89 |
| Manganese[1] | 0.81 | 95 | 87 |
| Iron[2] | 0.09 | 79 | 75 |
| Chromium[2] | 0.02 | 79 | 69 |
| Sodium[3] | 0.12 | 92 | 89 |

[1]Component of oxidation catalyst reported as element.
[2]Metals of corrosion of apparatus elements.
[3]Contaminant metal from washing of apparatus.

In the above table, the ions (organic or inorganic) associated with the six elements shown have not been taken into account. Thus the sum of the numbers shown in the column headed "Wt. % of Residue" is not 100%. Although the major (68 wt. %) component in the residue extracted was phthalic anhydride, the component in the extract solution was, of course, o-phthalic acid. In calculating the selectivity of its extraction, its equivalents were taken into account.

TABLE IV

EXTRACTION AT 77° C., FILTRATION AT 24° C. WITH WATER TO RESIDUE WEIGHT RATIO OF 1:1 USING RESIDUE FROM DEHYDRATION-EVAPORATION OF FLUID EFFLUENT FROM NEAT OXIDATION OF ORTHO-XYLENE

| Residue Components | Wt. % of Residue | Component in Filtrate Wt. % | Wt. % from Residue |
|---|---|---|---|
| Benzoic Acid | 1.8 | 0.2 | 29 |
| o-Toluic Acid | 0.1 | 0.003 | 8 |
| Phthalide | 0.3 | 0.05 | 43 |
| Phthalic Anhydride (Acid) | 57.3 | (7.2) | (33) |
| Iso- and Terephthalic Acid | 0.9 | 0.2 | 59 |
| Trimellitic Anhydride (Acid) | 4.0 | (1.5) | (100) |
| Other High Boilers[1] | 17.8 | 7.6 | 113 |
| Bromine | 1.01[2] | 0.31[2] | 81 |
| Cobalt | 0.58 | 0.24 | 110 |
| Manganese | 1.13 | 0.5 | 117 |
| Iron | 0.036 | 0.013[2] | 99 |
| Chromium | 0.011 | 0.004[2] | 95 |
| Nickel | 0.007 | 0.004[2] | 150 |
| Sodium | 0.093 | 0.045 | 128 |

[1]Compounds boiling higher than trimellitic anhydride including dicarboxynaphthalene, methyldicarboxybenzophenone, tricarboxybenzophenone, and bis(carboxyanthraquinone).
[2]Analysis by X-ray fluorescence; all other elements by atomic absorption.

EXAMPLE 1

Conduct of the present invention is illustrated by the following examples wherein the aqueous extract (24° C.) of trimellitic acid process residue (water to residue ratio of 2:1.0) is placed in a cylinder closed at its bottom with a cation permeable membrane film of polytetrafluoroethylene modified by sulfonic acid groups attached to chain carbon atoms. Said cylinder is placed with its film covered bottom down in a chamber which contains hydrochloric acid (37 wt. % HCl). Both the extract solution and the hydrochloric acid are stirred. The catalyst metals content in grams initially in the aqueous solution, finally in the hydrochloric acid and remaining in the depleted aqueous solution are reported in TABLE V below:

TABLE V

EXTRACTION OF METALS FROM AQUEOUS SOLUTION BY CATION PERMEABLE FLUOROPOLYMER MEMBRANE

| | Cobalt | Manganese | Cerium |
|---|---|---|---|
| Initial H₂O Solution | 0.115 | 0.065 | 0.06 |
| Final HCl Solution | 0.089 | 0.048 | 0.052 |
| Depleted H₂O Solution | 0.026 | 0.017 | 0.008 |

The foregoing demonstrates that about 77% of the cobalt, 74% of the manganese and 87% of the cerium passed through the membrane and into the hydrochloric acid.

EXAMPLE 2

The residue from the manufacture of isophthalic acid is extracted with equal weight parts of water at 25° C. The aqueous extract solution is fed into the coil of cation permeable fluoropolymer described in Example 1 whose exterior tube wall is in contact with hydrochloric acid (37 wt. % HCl) for two hours at room temperature, about 25° C. The resulting hydrochloric acid was analyzed for manganese and cobalt. From such analysis 22% of the manganese and 5% of the cobalt had migrated from the extract solution to the hydrochloric acid.

EXAMPLES 3 and 4

The residue from the manufacture of terephthalic acid is extracted with water at 24° C. with a water to residue weight ratio of 1:1. Said solution is divided into two equal parts. One part at 25° C. is fed to a coil of cation permeable fluoropolymer membrane described in Example 1 whose outer tube wall is in contact with 25° C. hydrochloric acid (37% HCl). The second part of the extract solution is heated to 50° C. and fed to a second such coil of cation permeable fluoropolymer membrane in contact with hydrochloric acid (37 wt. % HCl) at 50° C. The time of contact is two hours for each extract solution.

Contact at 25° C. caused 22% of the manganese and 15% of the cobalt to migrate to the hydrochloric acid solution.

Contact at 50° C. causes 62% of the manganese and 51% of the cobalt to migrate to the hydrochloric acid solution.

Optimum migration of cobalt and manganese from the aqueous extract solution from residue of terephthalic acid manufacture appears to be between 75° and 90° C.

EXAMPLE 5

The catalyst metals cobalt, manganese and cerium are separated from residue, fluid when made, from the manufacture of trimellitic acid in a continuous flow system in the following manner.

The hot (200° C.) fluid residue at 2.4 kg per hour is mixed with 2.4 kg per hour of water at a temperature of 24° C. The resulting slurry of insolubles suspended in extract solution cooled to 100° C. by indirect heat exchange is pumped through coils of cation permeable fluoropolymer tubing described in Examples 2 through 4 in a vessel and surrounded by hydrochloric acid (30 wt. % HCl) flowing through the vessel at 4 kg per hour. The outflow of hydrochloric acid containing the catalyst metals passing through the cation permeable polymeric tubing amounts to 5.0 kg per hour. Such outflow hydrochloric acid is contacted in indirect heat exchange with the slurry of insoluble suspended in extract solution whereby 4.0 kg per hour of hydrochloric acid (HCl and water vapor) are driven off, condensed and recycled to the catalyst metal permeation exchange. The remaining 1.0 kg of solution contains the catalyst metals as chloride solutes. The effluent from the cation permeable tubes amounts to 4.6 kg per hour, is essentially metal free and is useful as feed to an evaporation system conducted in one or two series-connected wiped film evaporators for removal of solvent water and water of dehydration of trimellitic acid to its intramolecular anhydride and evaporation of said anhydride and lower boiling organic impurities from higher boiling impurities. Then by either partial condensation or a combination of total condensation and distillation trimellitic acid anhydride (4-carboxyphthalic anhydride) in an amount of about 0.6 kg per hr. can be recovered.

The invention claimed is:

1. The separation of ions of cobalt, manganese cerium or combinations of said metal ions from a residue from the manufacture of a benzene carboxylic acid wherein one or all of said metals is used as metal oxidation catalyst, which separation comprises extracting the residue with from 0.5 up to 6 weight parts of water per weight part of residue at a temperature of from 25° C: up to 100° C. and then at a temperature from 25° C. up to 100° C. contacting the extract solution or the suspension of insolubles in said solution with one side of a cation permeable fluoropolymer membrane whose other side is in contact with hydrochloric or hydrobromic acid.

2. The separatory method of claim 1 wherein the cation permeable membrane is a polyfluoroethylene modified by sulfonic acid groups attached to chain carbon atoms.

3. The separation method of claim 2 wherein the water to residue weight ratio is 0.35:1.0 up to 3.0:1.

4. The separation method of claim 3 wherein the hydrohalidic acid is hydrobromic acid.

5. The separation method of claim 3 wherein the hydrohalidic acid is hydrochloric acid.

6. The separation method of claim 5 wherein the cation permeable fluoropolymer membrane is in tubular form and the cation movement is from inside the tube through its wall and to the hydrochloric acid in contact with the external surface of the tube.

7. The separation method of claim 5 wherein the weight ratio of water to residue is 0.35:1.0 to 1.0:1.0 and the cation permeable fluoropolymer membrane is in tubular form and the cation movement is from inside the tube through its wall to the hydrochloric acid in contact with the external wall of the tube.

* * * * *

UNITED STATES PATENT OFFICE
CERTIFICATE OF CORRECTION

Patent No. 4,312,778            Dated January 26, 1982

Inventor(s) Jon J. Harper

It is certified that error appears in the above-identified patent and that said Letters Patent are hereby corrected as shown below:

Patent reads:

| Col. | Line | | |
|---|---|---|---|
| 2 | 26 | "at at 80°C." should read | --at 80°C-- |
| 3 | 33 | "sufonyl, suffinyl" should read | --sulfonyl, sulffinyl-- |
| 8 | 15 | "manganese cerium" should read | --manganese, cerium-- |

Signed and Sealed this

Twenty-ninth Day of June 1982

[SEAL]

Attest:

GERALD J. MOSSINGHOFF

Attesting Officer     Commissioner of Patents and Trademarks